US007148064B1

(12) United States Patent
Georges et al.

(10) Patent No.: US 7,148,064 B1
(45) Date of Patent: Dec. 12, 2006

(54) METHOD FOR REDUCING PHYTATE IN CANOLA MEAL USING GENETIC MANIPULATION INVOLVING MYO-INOSITOL 1-PHOSPATHE SYNTHASE GENE

(75) Inventors: Fawzy Georges, Saskatoon (CA); Atta A. Hussain, Saskatoon (CA); Wilfred A. Keller, Saskatoon (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/979,776

(22) PCT Filed: May 25, 2000

(86) PCT No.: PCT/CA00/00612

§ 371 (c)(1),
(2), (4) Date: Mar. 1, 2002

(87) PCT Pub. No.: WO00/73473

PCT Pub. Date: Dec. 7, 2000

Related U.S. Application Data

(60) Provisional application No. 60/136,204, filed on May 26, 1999.

(51) Int. Cl.
C12N 15/29 (2006.01)
C12N 15/82 (2006.01)
C12N 15/87 (2006.01)
C12N 5/04 (2006.01)

(52) U.S. Cl. .................... 435/419; 435/410; 435/320.1; 800/306; 536/24.1

(58) Field of Classification Search ............... 536/23.1, 536/23.6, 24.1, 24.5; 800/298, 290, 278, 800/285; 435/468, 320.1
See application file for complete search history.

(56) References Cited

U.S. PATENT DOCUMENTS 5,712,112 A * 1/1998 Yu et al. .................... 435/69.1
5,750,871 A * 5/1998 Moloney et al. ............ 800/294
5,907,086 A * 5/1999 Neill et al. ................. 800/295
5,907,806 A * 5/1999 Yamada et al. ............. 455/434

FOREIGN PATENT DOCUMENTS

| GB | 1 480 857 A | 7/1977 |
|---|---|---|
| WO | 91 14782 A | 10/1991 |
| WO | 98 05785 A | 2/1998 |
| WO | 98 45448 A | 10/1998 |
| WO | 99 05298 A | 2/1999 |
| WO | 99 07211 A | 2/1999 |
| WO | 99 37786 A | 7/1999 |
| WO | 00 11177 A | 3/2000 |

OTHER PUBLICATIONS

Colliver et al (1997, Plant Mol. Biol. 35:509-522).*
Montgomery et al (Trends in Genetics, Jul. 1998, 14(7):255-258).*
Oommenn et al (1994, The Plant Cell 6:1789-1803).*
Benfey et al (1990, Science 250:959-966).*
Benfey et al (1989, EMBO J, 8(8):2195-2202).*
Napoli et al (1990 The Plant Cell 2:279-289).*
Keller et al (1998, The Plant Journal 16(4):403-410).*
Database EMBL 'Online!, Accession No.: U66307, Aug. 30, 1986 Hussain, A., et al.: XP002148805—& Database GENBANK 'Online!, GI:1513228 GENPEPT, Sep. 29, 1996 Hussain, A., et al.: XP002148806.
Thies W: "Determination of the Phytic Acid and Sinapic Acid Esters in Seeds of Rapeseed and Selection of Genotypes With Reduced Concentrations of These Compounds", Fett Wissenschaft Technologie, vol. 93, No. 2, 1991, pp. 49-52, XP002148802, ISSN: 0931-5985.
Database WPI, Section Ch, Week 199938, Derwent Publications Ltd., London, GB; AN 1999-451546, XP002148809 & JP 11 187879 A (Japan Tabacco Inc), Jul. 13, 1999, abstract—& Database GENESES 'Online!, Accession No.: X90402, Sep. 24, 1999, XP002148807.
Keller, Ruth et al: "Reduced inositol content and altered morphology in transgenic potato plants inhibited for 1D-myo-inositol 3-phosphate synthase.", Plant Journal, vol. 16, No. 4, Nov. 1998, pp. 403-410, XP002148803, ISSN: 0960-7412.
Mahajan Anupama et al: "Nonchemical approach for reducing antinutritional factors in rapeseed (*Brassica campestris* Var. Torja) and characterization of enzyme phytase.", Journal of Agricultural and Food Chemistry, vol. 45, No. 7, 1997, pp. 2504-2508, XP002148804, ISSN: 0021-8561.
Database BIOSIS 'Online!, Biosciences Information Service, Philadelphia, PA, US; 1995, Al-Asheh S et al: "The effect of phosphate concentration on phytase production and the reduction of phytic acid content in canola meal by Aspergillus carbon arius during a solid-state fermentation process.", Database accession No. PREV199598233968, XP002148808, abstract, & Applied Microbiology and Biotechnology, vol. 43, No. 1, 1995, pp. 25-30, ISSN: 0175-7598.

* cited by examiner

Primary Examiner—Stuart F. Baum
(74) Attorney, Agent, or Firm—Pearne & Gordon LLP

(57) ABSTRACT

A plant, multicellular fragment of said plant or seed of said plant transformed with a nucleotide sequence of SEQ ID NO 1 or an allelic variant or a fragment thereof or a genetic equivalent thereof according to the degeneracy of the genetic code coding for a peptide having a *Brassica* myo-inositol 1-phosphate synthase activity, said plant, multicellular fragment or seed having reduced myo-inositol 1-phosphate synthase activity when compared with an equivalent untransformed plant, multicellular fragment or seed, such that there is reduced phytate present in the plant, multicellular fragment or seed. The invention also provides a method for reducing phytate in *Brassica*, which method comprises growing a *Brassica* plant comprising one of a myo-inositol 1-phosphate synthase antisense sequence and a myo-inositol 1-phosphate synthase cosuppression sequence thereby yielding a reduced amount of myo-inositol 1-phosphate synthase and consequently reduced phytate in said *Brassica*.

3 Claims, 1 Drawing Sheet

SEQ ID NO: 1 aaaccacaca aactcgattc aattaaaaac cgagaaaaca aaagtctgtt taaaagatgt tcatcgagag cttcaaagtc
gagagcccga acgtgaagta cacggagaat gagattcatt cggtgtacga ttacgagacc acggaggtcg
ttcacgagaa cgtcaacggt gcttaccagt ggatcgtgaa gcccaaggtt gtcaaatacg atttcaaaac cgacactcgt
gtcccaaat tagggttat gcttgttggt tggggaggaa acaatggatc aaccctcacc gctggtgtaa ttgccaataa
agaaggaatc tcgtgggcga ccaaggacaa ggtgcaacaa gcgaactact tcgggtcgtt aacacaagca tcgtctattc
gtgtcggatc ctttaacggt gaagagatgt atgcccctt caagagtctc gttccaatgg tgaatccgga tgatgttgtg
tttggaggat gggacataag cgatatgaat ttagcagacg cgatgggtag agccaaggtt cttgacattg atctgcagaa
acagctcagg ccttacatgg agaacattgt cccactccct gggatctacg accctgattt catcgctgcc aatcaaggct
cacgtgccaa caacgtgatc aaaggtacca agaaggaaca agtcgaccaa atcatcaagg acatgaggga
gtttaaggag aagaacaagg tggataaggt tgtggttctg tggacggcta acacagagcg ttacagcaat gtgatcgtgg
ggctaaacga cactatggag aatcttatga actctgtgga tagggatgag tctgagatct ctccttccac gctttatgct
attgcatgtg ttcttgaagg tattccttc atcaatggaa gccctcagaa caccttgtt ccgggtctta ttgatttggc
tatcaagaac aatgtttga tcggtggaga tgacttcaag agtggtcaaa ccaagatgaa atctgtcttg gttgatttcc
ttgttggtgc aggcatcaag cctacttcaa ttgtgagcta caatcaccta gggaacaacg atggaatgaa cctctcagct
ccacagacat tcagatctaa ggagatctcc aaaagtaatg tggttgacga tatggttgct agcaacggta tcctcttcga
gcccggggaa catccagacc atgtagttgt catcaagtat gtaccgtatg ttgcagatag caagcgagcc atggatgagt
atacatcaga gatattcatg ggaggcaaga acacaattgt gatgcacaat acctgcgagg actctctctt
agctgctcca atcatcttgg atcttgttct cctcgctgaa atcagcacca ggattcagtt caaatccgag aaagagggga
agtttcattc tttccatcct gtggccacca aacttagcta tctcaccaag gcaccgctcg tgccgccggg aacaccggtg
gttaatgcgc tgtcgaagca gcgggctatg ctggagaata ttcttagggc gtgtgttggg ctggcgccgg agaacaatat
gatcttggaa tacaagtgaa cacgaagcgt ttaagagtct ttaattagcc ccaaatataa gacttctgtt tcttgtttt
tttaataaa tgtttaaaaa tatgaatgct tgtgtttca gagatcaaag agcttttaga ttgatctttg tagggtgtga
agttaccggt gtttctagta atccagatgg gctagtataa aaaaaaaaa a

SEQUENCE LISTING

```
<160> NUMBER OF SEQ ID NOS: 5

<210> SEQ ID NO 1
<211> LENGTH: 1781
<212> TYPE: DNA
<213> ORGANISM: Brassica napus

<400> SEQUENCE: 1
aaaccacaca aactcgattc aattaaaaac cgagaaaaca aaagtctgtt taaaagatgt      60
tcatcgagag cttcaaagtc gagagcccga acgtgaagta cacggagaat gagattcatt     120
cggtgtacga ttacgagacc acggaggtcg ttcacgagaa cgtcaacggt gcttaccagt     180
ggatcgtgaa gcccaaggtt gtcaaatacg atttcaaaac cgacactcgt gtccccaaat     240 tagggggttat gcttgttggt tggggaggaa acaatggatc aaccctcacc gctggtgtaa     300
ttgccaataa agaaggaatc tcgtgggcga ccaaggacaa ggtgcaacaa gcgaactact     360
tcgggtcgtt aacacaagca tcgtctattc gtgtcggatc ctttaacggt gaagagatgt     420 atgcccttt caagagtctc gttccaatgg tgaatccgga tgatgttgtg tttggaggat     480
gggacataag cgatatgaat ttagcagacg cgatgggtag agccaaggtt cttgacattg     540
atctgcagaa acagctcagg ccttacatgg agaacattgt cccactccct gggatctacg     600
accctgattt catcgctgcc aatcaaggct cacgtgccaa caacgtgatc aaaggtacca     660
agaaggaaca agtcgaccaa atcatcaagg acatgagga gtttaaggag aagaacaagg     720
tggataaggt tgtggttctg tggacggcta acacagagcg ttacagcaat gtgatcgtgg     780
ggctaaacga cactatggag aatcttatga actctgtgga tagggatgag tctgagatct     840
ctccttccac gctttatgct attgcatgtg ttcttgaagg tattcctttc atcaatggaa     900
gccctcagaa caccttttgt ccgggtctta ttgatttggc tatcaagaac aatgtttttga    960 tcggtggaga tgacttcaag agtggtcaaa ccaagatgaa atctgtcttg gttgatttcc    1020
ttgttggtgc aggcatcaag cctacttcaa ttgtgagcta caatcaccta gggaacaacg    1080
atggaatgaa cctctcagct ccacagacat tcagatctaa ggagatctcc aaaagtaatg    1140
```

```
tggttgacga tatggttgct agcaacggta tcctcttcga gcccgggaa catccagacc    1200 atgtagttgt catcaagtat gtaccgtatg ttgcagatag caagcgagcc atggatgagt   1260
atacatcaga gatattcatg ggaggcaaga acacaattgt gatgcacaat acctgcgagg   1320
actctctctt agctgctcca atcatcttgg atcttgttct cctcgctgaa atcagcacca   1380
ggattcagtt caaatccgag aaagagggga agtttcattc tttccatcct gtggccacca   1440
aacttagcta tctcaccaag gcaccgctcg tgccgccggg aacaccggtg gttaatgcgc   1500
tgtcgaagca gcgggctatg ctggagaata ttcttagggc gtgtgttggg ctggcgccgg   1560
agaacaatat gatcttggaa tacaagtgaa cacgaagcgt ttaagagtct ttaattagcc   1620
ccaaatataa gacttctgtt tcttgttttt ttttaataaa tgttttaaaa tatgaatgct   1680
tgtgttttca gagatcaaag agcttttaga ttgatctttg tagggtgtga agttaccggt   1740
gtttctagta atccagatgg gctagtataa aaaaaaaaa a                        1781
```

<210> SEQ ID NO 2
<211> LENGTH: 510
<212> TYPE: PRT
<213> ORGANISM: Brassica napus

<400> SEQUENCE: 2

```
Met Phe Ile Glu Ser Phe Lys Val Ser Pro Asn Val Lys Tyr Thr
 1               5                  10                  15

Glu Asn Glu Ile His Ser Val Tyr Asp Tyr Glu Thr Thr Glu Val Val
                20                  25                  30

His Glu Asn Val Asn Gly Ala Tyr Gln Trp Ile Val Lys Pro Lys Val
            35                  40                  45

Val Lys Tyr Asp Phe Lys Thr Asp Thr Arg Val Pro Lys Leu Gly Val
        50                  55                  60

Met Leu Val Gly Trp Gly Gly Asn Asn Gly Ser Thr Leu Thr Ala Gly
    65                  70                  75                  80

Val Ile Ala Asn Lys Glu Gly Ile Ser Trp Ala Thr Lys Asp Lys Val
                85                  90                  95

Gln Gln Ala Asn Tyr Phe Gly Ser Leu Thr Gln Ala Ser Ser Ile Arg
            100                 105                 110

Val Gly Ser Phe Asn Gly Glu Glu Met Tyr Ala Pro Phe Lys Ser Leu
        115                 120                 125

Val Pro Met Val Asn Pro Asp Asp Val Val Phe Gly Gly Trp Asp Ile
    130                 135                 140

Ser Asp Met Asn Leu Ala Asp Ala Met Gly Arg Ala Lys Val Leu Asp
145                 150                 155                 160

Ile Asp Leu Gln Lys Gln Leu Arg Pro Tyr Met Glu Asn Ile Val Pro
                165                 170                 175

Leu Pro Gly Ile Tyr Asp Pro Asp Phe Ile Ala Ala Asn Gln Gly Ser
            180                 185                 190

Arg Ala Asn Asn Val Ile Lys Gly Thr Lys Lys Glu Gln Val Asp Gln
        195                 200                 205

Ile Ile Lys Asp Met Arg Glu Phe Lys Glu Lys Asn Lys Val Asp Lys
    210                 215                 220

Val Val Val Leu Trp Thr Ala Asn Thr Glu Arg Tyr Ser Asn Val Ile
225                 230                 235                 240

Val Gly Leu Asn Asp Thr Met Glu Asn Leu Met Asn Ser Val Asp Arg
                245                 250                 255

Asp Glu Ser Glu Ile Ser Pro Ser Thr Leu Tyr Ala Ile Ala Cys Val
```

```
                    260                 265                 270
Leu Glu Gly Ile Pro Phe Ile Asn Gly Ser Pro Gln Asn Thr Phe Val
            275                 280                 285
Pro Gly Leu Ile Asp Leu Ala Ile Lys Asn Asn Val Leu Ile Gly Gly
            290                 295                 300
Asp Asp Phe Lys Ser Gly Gln Thr Lys Met Lys Ser Val Leu Val Asp
305                 310                 315                 320
Phe Leu Val Gly Ala Gly Ile Lys Pro Thr Ser Ile Val Ser Tyr Asn
                325                 330                 335
His Leu Gly Asn Asn Asp Gly Met Asn Leu Ser Ala Pro Gln Thr Phe
            340                 345                 350
Arg Ser Lys Glu Ile Ser Lys Ser Asn Val Val Asp Asp Met Val Ala
            355                 360                 365
Ser Asn Gly Ile Leu Phe Glu Pro Gly Glu His Pro Asp His Val Val
            370                 375                 380
Val Ile Lys Tyr Val Pro Tyr Val Ala Asp Ser Lys Arg Ala Met Asp
385                 390                 395                 400
Glu Tyr Thr Ser Glu Ile Phe Met Gly Gly Lys Asn Thr Ile Val Met
                405                 410                 415
His Asn Thr Cys Glu Asp Ser Leu Leu Ala Ala Pro Ile Ile Leu Asp
                420                 425                 430
Leu Val Leu Leu Ala Glu Ile Ser Thr Arg Ile Gln Phe Lys Ser Glu
            435                 440                 445
Lys Glu Gly Lys Phe His Ser Phe His Pro Val Ala Thr Lys Leu Ser
            450                 455                 460
Tyr Leu Thr Lys Ala Pro Leu Val Pro Pro Gly Thr Pro Val Val Asn
465                 470                 475                 480
Ala Leu Ser Lys Gln Arg Ala Met Leu Glu Asn Ile Leu Arg Ala Cys
                485                 490                 495
Val Gly Leu Ala Pro Glu Asn Asn Met Ile Leu Glu Tyr Lys
            500                 505                 510

<210> SEQ ID NO 3
<211> LENGTH: 36
<212> TYPE: DNA
<213> ORGANISM: Brassica napus

<400> SEQUENCE: 3
aaaaaatcta gagtgaacac ttgtattcca agatca                              36

<210> SEQ ID NO 4
<211> LENGTH: 33
<212> TYPE: DNA
<213> ORGANISM: Brassica napus

<400> SEQUENCE: 4
aaaaaacccg ggatgatcga gagcttcaaa gtc                                 33

<210> SEQ ID NO 5
<211> LENGTH: 3795
<212> TYPE: DNA
<213> ORGANISM: Brassica napus

<400> SEQUENCE: 5
taaattctag aacccacccc aaaaccaaaa aaaaactgga ccaaatgtga tgctataagc    60
ctactttaga tgcggaaaat tatggtcctt tacaaagatt tacctccttt agttgggata   120
```

-continued

```
tatgtggttt atagacgact aagatataa gcagtgtttt catacacgat ttaacccgca      180
gtcgaaacgg taaatttggt aaccatatat aatatggttt cgatttaatg aaaaaactca    240
ttaactaaaa atgcaataaa acctaaaaac ccgcaattaa cccgtgaacc gacacatgtt    300
gatccagtaa aatcccagaa aaatgtgatt aaactttca tactttttt attagtataa     360 aaaattaaat aaactatttg atttgtcata taaagtaaat acattgtatt tatgttatgc    420
attttagttt atgagttttg taatgatcat attaaagtta catttgtgag ttttgaaatt    480
aatatgagat tttaataatt ttagttatat tattataata taactatgta aatagatgaa    540 atctctttt ttaagtgaaa taggattctc ttacactctc agattttatg taaatatata     600
tatatatata tatatacact aacgtgtgtt gtgcactatt agtctattat aaatgtattt    660
gttaatgtca catactgaag gttagccaaa taaaaatgtc acacggttaa accattttgt    720
aacggttcct cgtttttaat gaataattat atatatgtca taagaatcaa accaatcggt    780
aatgttttgt ttgaattaat tgtaggacca aaataataac taatagtaat aaataggcca    840 aataatttt tgaagtagat ttattaaaac tccttccctt ttaatagtat tgatttctta     900
aatatggaaa ataagtatac ctcgaaatca tcggaaattt tattaaattt atgaatagta    960
gcatcaatta attaaaggat ttataacact gtacgaatct accagtatct ccggataata   1020
catagaaacg tccacgaaga aacctttat aaaggttgga aaagatttag aaccatttat    1080
gcgttaatta cttgatttaa tccgtttctg aacacttttc acacagacta aaaaagagc    1140 agaaatatac ggtaagttgt tattaaatta tattttctg accaaaagta ttttagataa    1200
ataaaattat ttataaaatc aatgcagttt acaataaatt ttcagttgaa agtaagtata   1260
atttgcattg aaattgtaaa ttgacatttt ttgtgtaaca aaaaaaaag caagaataat    1320 cacttgtcat agaacagtgg gagtatgata aaaactaatt ataaatgttc agacatatgt   1380
aagcttgtag attcaagtat ggtatagagc tcgacttcgg tcgtctcgag ctcgaactcg   1440
ccaaggtcga gatgcccgga ctcatggctt gccgtaccga gttcggccca tctcagccct   1500
tcaaaggcga tagaatcacc ggatctctcc acatgaccat ccaaaccgac gtcctcatcg   1560
agaccctaac cgccctcggc gctgaagtca gatggtgctc ctgcaacatc gtctacagaa   1620
gaagcctcct ccgattgtcg tgattcgctc aagtaaaagg agaaagcagc ggagagagga   1680
agagggtcgg accataaccc taattcccaa aatcacgagt cgattcgagg gtctggtggc   1740
gatgggtcgt cgaggtcggt ttcggttgcg gagagtgtcg tgtttggtaa agagaaggac   1800
tttaacggtg gaatgaacag agagctcgat ggcagtgaaa gcgtggtttc gttagtgcct   1860
tgtcgaagct ctggattgga gccatcatcc aaggtggttt cctcgcttgg agggacgacg   1920
cgctcgcgtg gaggccgtgg cgtgagaaga tcggattgca tgttcgagtt gtggttccgg   1980
gagatggagg ctaccacaga tctgtcgtcg ccggcttttc tccggggggt ggaggctcct   2040
tcagctccgc cgacgccggt tcaagttccc gggaaaggga gtcttcctta gatttaccttt  2100 cgcccggttt ggtgaacgga attgccggat gctttcatag atccgcgctg ccgatgagaa   2160
acccgaagct tttgggttaa ggttactatt gttcgtttag tgcgaaacta gaagtggtta    2220
ctgtctaggt ggttctgggt cagggcggag gagttctcgg tttgatgatg aagctctctg   2280
ctgaggtgaa gttggtcaag tcaacaatta ggtgattatc gatacgcacg tctagggttt   2340
taagcggttc aaaggcggag atgatctcgt gtttcgattg atctcttccg cgtgttgaca    2400
gtgcgggtag tggttggaag tttggttgtg tcggggata  tctcgatggt ttgagaaaga   2460
cctccgacat gatgtaaaag caaggaaaat agtctccggg gtgtgaaggt ggtcatgtgc    2520
```

```
                                                -continued cttaagccgc cggcaagtgg tttcctattt cctttctat gtattttta aggcttccaa    2580 tcttagtttc ttgcgtttaa gtcaagttgg ggttcgggtt tgttggataa agtttcttcg    2640
tcgtaggacg atggaagcta tccggagtaa aggttgttgc ttgagcgaag cctcctcctt    2700
tggtcctcgt attgaattct ggcggatgag atctcggtat cgattgattc tctctgacat    2760
taggcggtcc tgggaggttt ggcgttcgtg gtgaaaaagg tgaggagtct atgggctccg    2820
gtgaagcgta gtgaatcgat aggcgattct aaggtggttg ttgagttggt gcggttcgcg    2880
tgaaggcggc cgacatcacc ctttctctct tgggccggtg tagccttgtc ggcttacggt    2940
ttcgtttgtt tttgtttggt tgcccgttta gtgttgtggg cttttgtatt tgggcttcgg    3000
ccattgggct tggcccgtaa cttttaataa aataataact tgacggaaaa aaaaaaaaaa    3060
aaagcttgta gattcataat tcacgtgtca aagcaagtca acaagactcc acgggaccca    3120
actcaacgaa gacaaagagt caaaaaaacg gtcagacatt gttttcaaac gaccgttaat    3180
tagccacgtt agttactaca cgctccatct ctggaacgtg acatccaccc agaatatgtg    3240
gcagctaaat gtggtgtgtg tttacttcac tctcgttttt ttcgtaactg agaaacaact    3300
gtcgctaact aactgtaacg gagacaatgt ccgaaacact gtcgttttac tgattgagta    3360
acggaagtaa ctaacgtccc ccaccttgtt cgagcaccct caacaaaaaa atgtgggtcc    3420
gagaagacaa tccgacaaaa ctttgctatt gaaaaaacga cgccacgtgt atggtccagg    3480
gctccgacgt gtcacacttt ttctctccgc gcctctcacg tgcgagaccc ctccctcaca    3540
cgtatgattc actattagcc atcaacgaag tcgctcacat gcattggcta aagagggtcc    3600
accaaccact gagaccacgc cacgtgtctc ctctccctcg cgctcttttt ctataaatag    3660
cgctccattt aagagaagct caaacccaca caaactcgat tcaattaaaa accgagaaaa    3720
caaaagtctg tttaaaagat gttcatcgag agcttcaaag tcgagagccc gaacgtgaag    3780
tacacggaga atgag                                                   3795
```

METHOD FOR REDUCING PHYTATE IN CANOLA MEAL USING GENETIC MANIPULATION INVOLVING MYO-INOSITOL 1-PHOSPATHE SYNTHASE GENE

This application is the National Stage of International Application No. PCT/CA00/00612, filed May 25, 2000 which claims the benefit under 35 U.S.C. 119(e) of U.S. Provisional Application 60/136,204 filed May 26, 1999. This application was published in English on Dec. 7, 2000 as International Publication Number WO 00/73473 A1.

BACKGROUND OF THE INVENTION

The use of canola meal as an acceptable protein source in the animal feed industry is severely limited by the presence in the meal of undesirable seed contents such as glucosinolates, phytates, phenolics and hull. Phytate is a significant component of canola seeds, comprising up to 10% by weight of the seed. Phytic acid is the hexaphosphate derivative of myo-inositol. The presence of phytate has been linked to such symptoms as loss of appetite, reduced litter size and increase in the number of stillborn pups in rats. These effects have been attributed to the zinc-binding ability of phytic acid. The reduction of phytate in canola protein preparations has, to date, been difficult. Hence modification of its biosynthetic pathway to reduce its accumulation and enhance protein or oil synthesis in its place would be very significant in terms of the economic value of canola.

SUMMARY OF THE INVENTION

An aim of the present invention is to limit the utilization of myo-inositol as a starting material for phytic acid synthesis. This is complicated by the fact that myo-inositol is a crucial biological substrate, the presence of which is essential for the growth and multiplication of all living cells. In plants, for example, in addition to its participation in cell wall biogenesis, where myo-inositol furnishes a carbon source for uronides and pentoses, it is also present in phosphoinositides of plant cell membranes, as well as other complex plant lipids including glycophosphoceramides. Additionally, in some of its phosphorylated forms it acts as important second messengers in signal transduction pathways in eukaryotes. It is also a precursor of other naturally occurring inositol isomers and many of these as well as myo-inositol are distributed as methyl ethers in a species specific pattern throughout the plant kingdom.

In view of the vital role myo-inositol plays in plants, limiting its supply to the cell can be expected to promote reorganization of priorities within the cell, with possibly unforeseen consequences. Myo-inositol pathways leading to critical cell components or functions may be expected to proceed at the expense of other pathways that are of no direct and immediate consequence to the well-being of the plant during its life cycle. Phytic acid synthesis is an example of such a "futile" pathway since phytic acid is a storage substance that does not take part in any of the essential pathways during plant growth and development. It therefore seemed possible to us that, by limiting the availability of myo-inositol 1-phosphate synthase, lesser amounts of glucose 6-phosphate would be converted to myo-inositol thereby leading to a lower rate of phytic acid synthesis. It can be seen that a difficult balance has to be struck between over-limiting the production of myo-inositol thereby threatening critical pathways and under-limiting the production of myo-inositol with little consequent economic benefit.

The basic approach to limiting the rate of conversion of glucose 6-phosphate to myo-inositol 1-phosphate in *Brassica napus* was to prepare a mRNA transcript for the enzyme responsible for this step from *B. napus* and then to introduce a recombinant version of this gene into *Brassica* plants by, for example, *Agrobacterium*-mediated transformation in two different orientations (sense, for cosuppression, and antisense). Two particular types of constructs were produced containing either the 35S promoter or the seed-specific napin promoter. Integration of the construct into the genome was confirmed by Southern blot analysis. Phytic acid analysis showed reduction in levels of around 30% to 50% for antisense and cosuppression transgenic plants.

The invention provides a nucleotide sequence of SEQ ID NO 1 or an allelic variant or a fragment thereof or a genetic equivalent thereof according to the degeneracy of the genetic code coding for a peptide having a *Brassica* myo-inositol 1-phosphate synthase activity.

In preferred embodiments the nucleotide sequence, variant or fragment of the invention is in combination with a promoter sequence in reading frame alignment (preferably antisense) therewith.

The invention also provides a myo-inositol 1-phosphate synthase-active peptide sequence encoded by the nucleotide sequence of the invention. The invention also provides cells (preferably *Brassica*, especially *B. napus* cells) transformed with a nucleotide sequence of the invention. The invention further provides plants, multicellular fragments of such plants and seeds of such plants transformed with a nucleotide of the invention, the plant, multicellular fragment or seed having reduced myo-inositol 1-phosphate synthase activity such that there is reduced phytate present in the plant, multicellular fragment or seed. The multicellular fragment is preferably in the form of a seed meal.

The invention also provides a method for reducing phytate in *Brassica* which comprises limiting the availability of myo-inositol 1-phosphate synthase in said *Brassica* with one of one of a myo-inositol 1-phosphate synthase antisense sequence and a myo-inositol 1-phosphate synthase cosuppression sequence to give a reduced amount of translatable myo-inositol 1-phosphate synthase thereby reducing phytate in said *Brassica*. Preferably the *Brassica* is *Brassica napus*. The invention also provides a method for reducing phytate in *Brassica*, which method comprises growing a *Brassica* plant comprising one of a myo-inositol 1-phosphate synthase antisense sequence and a myo-inositol 1-phosphate synthase cosuppression sequence thereby yielding a reduced amount of myo-inositol 1-phosphate synthase and consequently reduced phytate in said *Brassica*.

DESCRIPTION OF THE SEQUENCE LISTING

SEQ ID NO: 1 shows the nucleotide sequence of a myo-inositol 1-phosphate synthase gene of *Brassica napus*.

SEQ ID NO: 2 show the amino acid sequence of my-inositol 1-phosphate synthase of *Brassica napus*.

SEQ ID NO: 3 shows the myo-inositol 1-phosphate synthase right primer used in the examples.

SEQ ID NO: 4 shows the myo-inositol 1-phosphate synthase left primer used in the examples.

SEQ ID NO: 5 shows a sequence comprising the myo-inositol 1-phosphate synthase (mips) promoter sequence used in the examples.

DESCRIPTION OF THE DRAWINGS

FIG. 1 shows the nucleotide sequence of the *Brassica napus* myo-inositol 1-phosphate synthase of the invention.

DETAILED DESCRIPTION OF THE INVENTION

As used herein, the term "functional fragments" when used to modify a specific gene or gene product means a less than full length portion of the gene or gene product which retains substantially all of the biological function associated with the full length gene or gene product to which it relates. To determine whether a fragment of a particular gene or gene product is a functional fragment, fragments are generated by well-known nucleolytic or proteolytic techniques or by the polymerase chain reaction and the fragments tested for the described biological function.

As used herein, a coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

As used herein, a "replicon" is any genetic element (e.g., plasmid, chromosome, virus) that functions as an autonomous unit of DNA replication in vivo; i.e., capable of replication under its own control.

As used herein, a "vector" is a replicon, such as a plasmid, phage, or cosmid, to which another DNA segment may be attached so as to bring about the replication of the attached segment.

As used herein, a "reference" gene refers to the wild type gene sequence of the invention and is understood to include the various sequence polymorphisms that exist, wherein nucleotide substitutions in the gene sequence exist, but do not affect the essential function of the gene product.

As used herein, a "mutant" gene refers sequences different from the reference gene wherein nucleotide substitutions and/or deletions and/or insertions result in perturbation of the essential function of the gene product.

As used herein, a DNA "coding sequence of" or a "nucleotide sequence encoding" a particular protein, is a DNA sequence which is transcribed and translated into a polypeptide when placed under the control of appropriate regulatory sequences.

As used herein, a "promoter sequence" is a DNA regulatory region capable of binding RNA polymerase in a cell and initiating transcription of a downstream (3' direction) coding sequence. For purposes of defining the present invention, the promoter sequence is bound at its 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

As used herein, DNA "control sequences" refers collectively to promoter sequences, ribosome binding sites, polyadenylation signals, transcription termination sequences, upstream regulatory domains, enhancers and the like, which collectively provide for the expression (i.e., the transcription and translation) of a coding sequence in a host cell.

As used herein, a control sequence "directs the expression" of a coding sequence in a cell when RNA polymerase will bind the promoter sequence and transcribe the coding sequence into mRNA, which is then translated into the polypeptide encoded by the coding sequence.

As used herein, a "host cell" is a cell which has been transformed or transfected, or is capable of transformation or transfection by an exogenous DNA sequence.

As used herein, a cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

As used herein, "transfection" or "transfected" refers to a process by which cells take up foreign DNA and integrate that foreign DNA into their chromosome. Transfection can be accomplished, for example, by various techniques in which cells take up DNA (e.g., calcium phosphate precipitation, electroporation, assimilation of liposomes, etc.) or by infection, in which viruses are used to transfer DNA into cells.

As used herein, a "target cell" is a cell that is selectively transfected over other cell types (or cell lines).

As used herein, a "clone" is a population of cells derived from a single cell or common ancestor by mitosis. A "cell line" is a clone of a primary cell that is capable of stable growth in vitro for many generations.

As used herein, a "heterologous" region of a DNA construct is an identifiable segment of DNA within or attached to another DNA molecule that is not found in association with the other molecule in nature. Thus, when the heterologous region encodes a gene, the gene will usually be flanked by DNA that does not flank the gene in the genome of the source. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

An aspect of the present invention is isolated polynucleotides encoding a protein including substantially similar sequences and functional fragments. Isolated polynucleotide sequences are substantially similar if they are capable of hybridizing under moderately stringent conditions to SEQ ID NO:1 or they encode DNA sequences which are degenerate to SEQ ID NO:1 or are degenerate to those sequences capable of hybridizing under moderately stringent conditions to SEQ ID NO:1.

Moderately stringent conditions is a term understood by the skilled artisan and has been described in, for example, Sambrook et al. Molecular Cloning: A Laboratory Manual, 2nd edition, Vol. 1, pp. 101–104, Cold Spring Harbor Laboratory Press (1989). An exemplary hybridization protocol using moderately stringent conditions is as follows. Nitrocellulose filters are prehybridized at 65.degree. C. in a solution containing 6.times. SSPE, 5.times. Denhardt's solution (10 g Ficoll, 10 g BSA and 10 g polyvinylpyrrolidone per liter solution), 0.05% SDS and 100 µg/ml tRNA. Hybridization probes are labelled, preferably radiolabelled (e.g., using the Bios TAG-IT.RTM. kit). Hybridization is then carried out for approximately 18 hours at 65.degree. C. The filters are then washed twice in a solution of 2.times. SSC and 0.5% SDS at room temperature for 15 minutes. Subsequently, the filters are washed at 58.degree. C., air-dried and exposed to X-ray film overnight at −70.degree. C. with an intensifying screen.

Degenerate DNA sequences encode the same amino acid sequence as SEQ ID NO:2 or the proteins encoded by that sequence capable of hybridizing under moderately stringent conditions to SEQ ID NO:1, but have variation(s) in the nucleotide coding sequences because of the degeneracy of the genetic code. For example, the degenerate codons UUC and UUU both code for the amino acid phenylalanine, whereas the four codons GGX all code for glycine.

Alternatively, substantially similar sequences are defined as those sequences in which about 70%, preferably about 80% and most preferably about 90%, of the nucleotides or amino acids match over a defined length of the molecule. As used herein, substantially similar refers to the sequences having similar identity to the sequences of the instant invention. Thus nucleotide sequences that are substantially the same can be identified by hybridization or by sequence comparison. Protein sequences that are substantially the same can be identified by techniques such as proteolytic digestion, gel electrophoresis and/or microsequencing.

Embodiments of the isolated polynucleotides of the invention include DNA, genomic DNA and RNA, preferably of *Brassica* origin. A method for isolating a nucleic acid molecule encoding a protein is to probe a genomic or cDNA library with a natural or artificially designed probe using art recognized procedures. See, e.g., "Current Protocols in Molecular Biology", Ausubel et al. (eds.) Greene Publishing Association and John Wiley Interscience, New York, 1989, 1992. The ordinarily skilled artisan will appreciate that SEQ ID NO:1 or fragments thereof comprising at least 15 contiguous nucleotides are particularly useful probes. It is also appreciated that such probes can be and are preferably labelled with an analytically detectable reagent to facilitate identification of the probe. Useful reagents include, but are not limited to, radioisotopes, fluorescent dyes or enzymes capable of catalysing the formation of a detectable product. The probes would enable the ordinarily skilled artisan to isolate complementary copies of genomic DNA, cDNA or RNA polynucleotides encoding proteins from *Brassica* or other plant sources or to screen such sources for related sequences, e.g., additional members of the family, type and/or subtype, including transcriptional regulatory and control elements as well as other stability, processing, translation and tissue specificity-determining regions from 5' and/or 3' regions relative to the coding sequences disclosed herein, all without undue experimentation.

Another aspect of the invention is functional polypeptides encoded by the polynucleotides of the invention. An embodiment of a functional polypeptide of the invention is the *Brassica* protein having the amino acid sequence set forth in SEQ ID NO:2.

Another aspect of the invention is a method for preparing essentially pure *Brassica* protein. Yet another aspect is the *Brassica* protein produced by the preparation method of the invention. This protein has the amino acid sequence listed in SEQ ID NO:2 and includes variants with a substantially similar amino acid sequence that have the same function. The proteins of this invention can be made by recombinant genetic engineering techniques by culturing a recombinant host cell containing a vector encoding the polynucleotides of the invention under conditions promoting the expression of the protein and recovery thereof.

The isolated polynucleotides, particularly the DNAs, can be introduced into expression vectors by operatively linking the DNA to the necessary expression control regions, e.g., regulatory regions, required for gene expression. The vectors can be introduced into an appropriate host cell such as a prokaryotic, e.g., bacterial, or eukaryotic, e.g., yeast or plant cell by methods well known in the art. See Ausubel et al., supra. The coding sequences for the desired proteins, having been prepared or isolated, can be cloned into any suitable vector or replicon. Numerous cloning vectors are known to those of skill in the art and the selection of an appropriate cloning vector is a matter of choice. Examples of recombinant DNA vectors for cloning and host cells which they can transform include, but are not limited to, the bacteriophage lambda. (*E. coli*), pBR322 (*E. coli*), pACYC177 (*E. coli*), pGEX4T-3 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtlilis*), pBD9 (*Bacillus*), pIJ61 (*Streptomyces*), pUC6 (*Streptomyces*), YIp5 (*Saccharomyces*) and YCp19 (*Saccharomyces*). See generally, "DNA Cloning": Vols. I & II, Glover et al. ed. IRL Press Oxford (1985) (1987); and T. Maniatis et al. ("Molecular Cloning" Cold Spring Harbor Laboratory (1982).

The gene can be placed under the control of control elements such as a promoter, ribosome binding site (for bacterial expression) and, optionally, an operator, so that the DNA sequence encoding the desired protein is transcribed into RNA in the host cell transformed by a vector containing the expression construct. The coding sequence may or may not contain a signal peptide or leader sequence. The proteins of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437 and 4,338,397.

In addition to control sequences, it may be desirable to add regulatory sequences which allow for regulation of the expression of the protein sequences relative to the growth of the host cell. Regulatory sequences are known to those of skill in the art. Exemplary are those which cause the expression of a gene to be turned on or off in response to a chemical or physical stimulus, including the presence of a regulatory compound or to various temperature or metabolic conditions. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences, i.e., RNA polymerase which binds to the DNA molecule at the control sequences transcribes the coding sequence. Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to produce mutants or analogues of Brassica protein. Mutants or analogues may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; "DNA Cloning," Vols. I and II, supra; and "Nucleic Acid Hybridization", supra.

Depending on the expression system and host selected, the proteins of the present invention are produced by growing host cells transformed by an expression vector described above under conditions whereby the protein of interest is expressed. Preferred plant cells include Brassica cells. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform E. coli and pooling and screening individual colonies.

The proteins of the present invention may also be produced by chemical synthesis such as solid phase peptide synthesis on an automated peptide synthesizer, using known amino acid sequences or amino acid sequences derived from the DNA sequence of the genes of interest. Such methods are known to those skilled in the art.

Another aspect of the invention is antisense oligonucleotides comprising a sequence which is capable of binding to the polynucleotides of the invention. Synthetic oligonucleotides or related antisense chemical structural analogs can be designed to recognize, specifically bind to and prevent transcription of a target nucleic acid encoding protein by those of ordinary skill in the art. See generally, Cohen, J. S., Trends in Pharm. Sci., 10, 435(1989) and Weintraub, H. M., Scientific American, January (1990) at page 40. By "antisense" RNA is meant a complementary RNA sequence that binds to and blocks the transcription of a naturally occurring sense messenger RNA molecule.

By "cosuppression" is meant the phenomenon of native gene silencing as a result of attempting to over-express the same gene, by recombinant DNA, in its original host plant (from which the gene has been isolated). In the case of this invention the myo-inositol 1-phosphate (mips) gene was isolated from Brassica napus and was re-introduced back into B. napus by Agrobacterium tumefasciens transformation.

Defining appropriate hybridization conditions is within the skill of the art. See, e.g., "Current Protocols in Mol. Biol." Vol. I & II, Wiley Interscience. Ausbel et al. (eds.) (1992). Probing technology is well known in the art and it is appreciated that the size of the probes can vary widely but it is preferred that the probe be at least 15 nucleotides in length. It is also appreciated that such probes can be and are preferably labelled with an analytically detectable reagent to facilitate identification of the probe. Useful reagents include but are not limited to radioisotopes, fluorescent dyes or enzymes capable of catalysing the formation of a detectable product. As a general rule, the more stringent the hybridization conditions the more closely related genes will be that are recovered.

Another aspect of the invention is transgenic, non-Brassica plants capable of expressing the polynucleotides of the invention in any cell. Transgenic, non-Brassica plants may be obtained by transfecting with the polynucleotides of the invention. The resultant transgenic plant may be used as a model for the study of gene function or for producing large amounts of protein for screening or crystallography purposes. Particularly useful transgenic plants are those which display a detectable phenotype associated with the expression of the protein.

Experimental Results a) Cloning of Myo-Inositol 1-Phosphate Synthase (MIPS) Gene from B. napus:

A cDNA copy of MIPS gene was isolated from B. napus developing seed by the RT-PCR method. RT-PCR was conducted by synthesizing 1st strand cDNA of MIPS using the 1st strand cDNA synthesis kit (Boehringer Mannheim). Briefly, 1 µg of total RNA from B. napus developing seeds was added to 0.5 ml tube containing MIPS-right primer (SEQ ID NO: 3–5' AAAAAATCTAGAGTGAACACTTG-TATTCCAAGATCA 3'), 1× RT (reverse transcriptase) buffer, the four dNTPs, and water. The mixture was incubated at 25° C. for 10 min and was then placed on ice. Subsequently, 20 U of RT (reverse transcriptase) was added, mixed very well. The reaction was initiated by incubating the tube at 42° C. for 60 min. Finally, heating at 95° C. for 10 min inactivated the RT enzyme. The product is the 1st strand of MIPS gene.

For PCR amplification, 5 µL of 1st strand cDNA solution was added to 0.5 ml tube containing 1× Vent polymerase buffer, the four dNTPs, the MIPS-left primer (SEQ ID NO: 4–5' AAAAAACCCGGGATGATCGAGAGCT-TCAAAGTC 3'), the right primer, and water. The reaction was initiated by addition of 1 U of Vent DNA polymerase, mixed very well and placed in a DNA thermal cycler (Perkin Elmer Cetus). Heating at 94° C. for 2 min followed by 35 cycle each of which includes heating at 94° C. for 1 min, annealing at 52° C. for 1 min and extension at 72° C. for 3 min.

The left and right primer (containing XbaI and SmaI site respectively) were synthesized according to the published MIPS DNA sequence of Arabidopsis thaliana (GenBank accession number U04876).

At the end of the PCR run, 5 µL of the reaction solution was loaded on 1.2% Agarose gel. The PCR product was purified by PCR purification kit (Promaga) and was then digested with both XbaI and SmaI. The digested DNA was loaded on gel and the 1.7 Kb fragment was eluted and purified. The purified fragment was then cloned into pSPORT1 (GIBGOBRL) pre-cut with both XbaI and SmaI. The clone containing the insert was subjected to full length DNA sequencing.

Total RNA was extracted from plant tissue by using RNeasy plant total RNA kit (Qiagen).

b) DNA Sequence Analysis

DNA sequencing was performed by the DNA Services Lab at PBI using ABI Prism Dye Terminator cycle sequencing ready reaction kit with AmpliTaq DNA polymerase and following the company's protocol (Perkin Elmer).

These primers as well as those for sequencing were synthesized in an Applied Biosystems DNA synthesizer.

c) Cloning of MIPS Gene in pBI121

The MIPS cDNA was cloned under CamV35S or *B. napus* napin promoters in both orientations (sense or anti-sense) in the plant vector pBI121 (from Clontech). The constructs were transferred into *Agrobacterium tumefaciens* strain CV3101: pMP90RK by electroporation. The transformants were grown on kanamycin-containing plates and then screened by PCR analysis for the presence of the construct. The positive transformants were used for *Brassica napus* transformation. Plant transformation was conducted according to Maloney et al, 1989 (Maloney, N. M., Walker, J M., and Sharma, K. K. 1989, Plant Cell Reports 8, 238)

d) Isolation of the MIPS Genomic Promoter

The genomic MIPS promoter was isolated from *B. napus* by PCR with a primer designed to read beyond the 5' end of the MIPS gene. The DNA sequence of this promoter probably extends much beyond the promoter itself. This promoter would be useful for targeting the expression of foreign genes to the same location and at the same time (spatial- and temporal-mode of expression). In this way more precise deactivation of MIPS gene can be achieved. Also, it can be used in any experiments where the desired trait must accompany the expression of the native MIPS gene. The sequence including the MIPS promoter (3795 bp) from *B. napus* that we cloned is shown in SEQ ID NO:5.

e) Plant Materials:

*Brassica napus*, Var. Westar, the control and transgenic, plants were grown in a growth-chamber under a 16 hr. light cycle at 20° C., followed by 8 hr. darkness at 15° C. Phytate levels were measured and compared for control and transgenic plants. Reductions of 30% to 50% in phytate levels were found.

The invention claimed is:

1. An isolated gene expression cassette comprising the *Brassica napus* myo-inositol-1-phosphate synthase gene promoter of SEQ ID NO:5 which is bound to and initiates transcription of myo-inositol-1-phosphate synthase coding sequence of SEQ ID NO:1 in co-suppression orientation.

2. A plant cell transformed with the isolated gene expression cassette according to claim 1.

3. A *Brassica* cell transformed with the isolated gene expression cassette according to claim 1.

* * * * *